US008523899B2

(12) United States Patent
Suzuki

(10) Patent No.: US 8,523,899 B2
(45) Date of Patent: Sep. 3, 2013

(54) TREATMENT DEVICE FOR ENDOSCOPE

(75) Inventor: Keita Suzuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/591,573

(22) Filed: Aug. 22, 2012

(65) Prior Publication Data

US 2012/0316543 A1 Dec. 13, 2012

Related U.S. Application Data

(63) Continuation of application No. PCT/JP2011/079816, filed on Dec. 22, 2011.

(30) Foreign Application Priority Data

Dec. 28, 2010 (JP) .................................. 2010-293229

(51) Int. Cl.
*A61B 17/29* (2006.01)

(52) U.S. Cl.
USPC .......................................... 606/205; 604/526

(58) Field of Classification Search
CPC ....................................................... A61B 17/29
USPC ........................................ 606/205; 604/526
See application file for complete search history.

(56) References Cited

U.S. PATENT DOCUMENTS

| 2,492,352 | A | * | 12/1949 | Bourdon | ........................... 57/215 |
| 3,267,697 | A | * | 8/1966 | Oldberg et al. | ................... 464/58 |
| 3,618,613 | A | * | 11/1971 | Schulte | ........................... 604/523 |
| 3,749,085 | A | * | 7/1973 | Willson et al. | ................. 600/570 |
| 3,749,086 | A | * | 7/1973 | Kline et al. | .................... 600/585 |
| 3,879,516 | A | * | 4/1975 | Wolvek | ........................... 264/135 |

(Continued)

FOREIGN PATENT DOCUMENTS

| JP | A-57-153629 | 9/1982 |
| JP | U-6-81504 | 11/1994 |

(Continued)

OTHER PUBLICATIONS

International Search Report issued in International Patent Application No. PCT/JP2011/079816 dated Jan. 31, 2012 (with translation).

(Continued)

*Primary Examiner* — Sam Yao
*Assistant Examiner* — Manolis Pahakis
(74) *Attorney, Agent, or Firm* — Oliff & Berridge, PLC

(57) ABSTRACT

Disclosed is a treatment device for an endoscope including a treatment part that is adapted to treat tissue within a body cavity, a manipulating part that is adapted to manipulate the treatment part, a manipulation shaft member that connects the treatment part and the manipulating part, a multi-wire coil sheath that is formed by spirally winding a wire bundle having a plurality of element wires arranged in a longitudinal direction, and a plurality of fixing portions that is arranged between a distal end and a proximal end of the multi-wire coil sheath and restricts a first relative movement between the plurality of element wires and a second relative movement between parts of the wire bundle that are adjacent to each other as being spirally wound. The manipulation shaft member is inserted into the multi-wire coil sheath so that the manipulation shaft member is capable of being advanced and retracted.

4 Claims, 8 Drawing Sheets

(56) References Cited

U.S. PATENT DOCUMENTS

| | | | | |
|---|---|---|---|---|
| 3,924,632 | A * | 12/1975 | Cook | 604/527 |
| 4,020,829 | A * | 5/1977 | Willson et al. | 600/434 |
| 4,493,329 | A * | 1/1985 | Crawford et al. | 607/125 |
| 4,538,622 | A * | 9/1985 | Samson et al. | 600/585 |
| 4,719,924 | A * | 1/1988 | Crittenden et al. | 600/585 |
| 4,721,116 | A * | 1/1988 | Schintgen et al. | 600/564 |
| 4,798,598 | A * | 1/1989 | Bonello et al. | 604/528 |
| 4,889,327 | A * | 12/1989 | Seyler | 267/168 |
| 4,899,787 | A * | 2/1990 | Ouchi et al. | 138/131 |
| 4,932,419 | A * | 6/1990 | de Toledo | 600/585 |
| 4,951,677 | A * | 8/1990 | Crowley et al. | 600/463 |
| 5,002,041 | A * | 3/1991 | Chikama | 600/139 |
| 5,019,057 | A * | 5/1991 | Truckai | 604/527 |
| 5,052,404 | A * | 10/1991 | Hodgson | 600/585 |
| 5,065,769 | A * | 11/1991 | de Toledo | 600/585 |
| 5,069,674 | A * | 12/1991 | Fearnot et al. | 604/524 |
| 5,137,013 | A * | 8/1992 | Chiba et al. | 606/205 |
| 5,176,660 | A * | 1/1993 | Truckai | 604/527 |
| 5,306,252 | A * | 4/1994 | Yutori et al. | 600/585 |
| 5,353,798 | A * | 10/1994 | Sieben | 600/462 |
| 5,429,597 | A * | 7/1995 | DeMello et al. | 604/509 |
| 5,438,997 | A * | 8/1995 | Sieben et al. | 600/463 |
| 5,441,516 | A * | 8/1995 | Wang et al. | 606/198 |
| 5,445,155 | A * | 8/1995 | Sieben | 600/443 |
| 5,630,806 | A * | 5/1997 | Inagaki et al. | 604/524 |
| 5,681,348 | A * | 10/1997 | Sato | 606/205 |
| 5,746,696 | A * | 5/1998 | Kondo | 600/139 |
| 5,762,995 | A * | 6/1998 | Kondo et al. | 427/2.12 |
| 5,766,197 | A * | 6/1998 | Porter | 606/170 |
| 5,873,866 | A * | 2/1999 | Kondo et al. | 604/526 |
| 5,885,207 | A * | 3/1999 | Iwasaka | 600/139 |
| 5,951,539 | A * | 9/1999 | Nita et al. | 604/526 |
| 5,971,940 | A * | 10/1999 | Baker et al. | 600/567 |
| 6,210,395 | B1 * | 4/2001 | Fleischhacker et al. | 604/526 |
| 6,290,692 | B1 * | 9/2001 | Klima et al. | 604/524 |
| 6,551,305 | B2 * | 4/2003 | Ferrera et al. | 606/1 |
| 6,589,227 | B2 * | 7/2003 | Sønderskov Klint | 604/524 |
| 6,777,644 | B2 * | 8/2004 | Peacock et al. | 219/121.72 |
| 6,896,671 | B2 * | 5/2005 | Vitullo et al. | 604/526 |
| 6,920,361 | B2 * | 7/2005 | Williams | 607/122 |
| 7,037,271 | B2 * | 5/2006 | Crowley | 600/463 |
| 7,158,837 | B2 * | 1/2007 | Osypka et al. | 607/122 |
| 7,182,735 | B2 * | 2/2007 | Shireman et al. | 600/585 |
| 7,413,543 | B2 * | 8/2008 | Banik et al. | 600/129 |
| 7,763,012 | B2 * | 7/2010 | Petrick et al. | 604/527 |
| 7,785,273 | B2 * | 8/2010 | Eskuri | 600/585 |
| 7,914,466 | B2 * | 3/2011 | Davis et al. | 600/585 |
| 7,998,150 | B2 * | 8/2011 | Shiono et al. | 606/144 |
| 2004/0006362 | A1 * | 1/2004 | Schaefer et al. | 606/200 |
| 2005/0049574 | A1 * | 3/2005 | Petrick et al. | 604/525 |
| 2005/0054952 | A1 * | 3/2005 | Eskuri et al. | 600/585 |
| 2008/0194910 | A1 * | 8/2008 | Miyamoto et al. | 600/104 |
| 2009/0247822 | A1 * | 10/2009 | Okada et al. | 600/106 |
| 2011/0071355 | A1 * | 3/2011 | Kura | 600/118 |
| 2011/0071564 | A1 * | 3/2011 | Suzuki | 606/205 |

FOREIGN PATENT DOCUMENTS

| | | |
|---|---|---|
| JP | A-2008-148738 | 7/2008 |
| JP | A-2008-212620 | 9/2008 |
| KR | 10-2008-0074759 A | 8/2008 |

OTHER PUBLICATIONS

Extended Search Report issued in European Patent Application No. 11853583.0 dated Oct. 8, 2012.

* cited by examiner

US 8,523,899 B2

TREATMENT DEVICE FOR ENDOSCOPE

FIELD OF THE INVENTION

The present invention relates to a treatment device for an endoscope that is inserted into a body cavity and is used for various procedures.

This application is a continuation application based on a PCT Patent Application No. PCT/JP2011/079816, filed Dec. 22, 2011, whose priority is claimed on Japanese Patent Application No. 2010-293229, filed in Japan on Dec. 28, 2010. The contents of both the PCT Application and the Japanese Application are incorporated herein by reference.

BACKGROUND ART

Conventionally, a treatment device for an endoscope including treatment parts, such as forceps, at the distal end thereof is known. When tissue within a body cavity is treated using such a treatment device for an endoscope, due to reasons such as the orientation of a treatment part that protrudes into the body not being suitable for the location of the target tissue to be treated, adjustment of the orientation of the treatment part may be required. In a case where such adjustment is performed, it is important to rotate the treatment part so as to exactly follow the manipulation of an operator.

Usually, in a case where the above-described treatment part is rotated, the manipulating part on the hand side of the treatment device for an endoscope is rotated. Here, in a case of a treatment device that pushes in manipulation wires connected to a treatment part such as forceps via a manipulating part to open and close the treatment part, a compressive force is applied in the axial direction of a coiled sheath together with the opening and closing. In this case, a multi-wire coil sheath around which a number of element wires are wound tends to become compressed in an axial direction, whereas the rotation transmissibility thereof is high compared to a single-line coiled sheath around which one element wire is wound. A displacement between the plurality of element wires (displacement of wires) may occur by this compression. Therefore, the coiled sheath is compressed in the axial direction, and an axial force to be transmitted to the distal end portion reduced, so that satisfactory treatment cannot be performed. As a result, the procedure becomes complicated.

In order to solve this problem, a treatment device for an endoscope described in Japanese Unexamined Patent Application, First Publication No. 2008-212620 is suggested. In this treatment device for an endoscope, a first coiled sheath around which one element wire is spirally wound is inserted through a second coiled sheath around which a plurality of element wires are spirally wound in the same direction. The distal end of the second coiled sheath is fixed to a movable distal end portion for performing treatment, and the proximal end of the second coiled sheath is fixed to a manipulating part.

In this way, using two types of coiled sheaths of the first coiled sheath and the second coiled sheath ensures a balance between a resistance to compression and a torque transmissibility.

SUMMARY OF THE INVENTION

The present invention has adopted the following means in order to solve the above problems and achieve the relevant objective.

That is, according to a treatment device for an endoscope related to a first aspect of the present invention, there is provided a treatment device for an endoscope including a treatment part that is adapted to treat tissue within a body cavity; a manipulating part that is adapted to manipulate the treatment part; a manipulation shaft member that connects the treatment part and the manipulating part; a multi-wire coil sheath that is formed by spirally winding a wire bundle having a plurality of element wires arranged in a longitudinal direction and through which the manipulation shaft member is inserted so that the manipulation shaft member can be advanced and retracted; and a plurality of the fixing portions that is arranged between a distal end and a proximal end of the multi-wire coil sheath and regulates a first relative movement between the plurality of element wires and a second relative movement between parts of the wire bundle that are adjacent to each other as being spirally wound.

According to a second aspect of the present invention, in the first embodiment, a plurality of the fixing portions may be provided, and the interval of the plurality of the fixing portions that is adjacent to each other may be 10 mm or more and 500 mm or less.

According to a third aspect of the present invention, in the first embodiment, the fixing portion may be formed by performing laser welding over a circumferential direction of the multi-wire coil sheath.

According to a fourth aspect of the present invention, in the first embodiment, the plurality of the fixing portions may be formed by performing laser welding over a circumferential direction of the multi-wire coil sheath.

Moreover, according to a fifth aspect of the present invention, in the first embodiment, a plurality of the fixing portions may be provided over the overall length of the multi-wire coil sheath.

DESCRIPTION OF EMBODIMENTS

Figure 1:
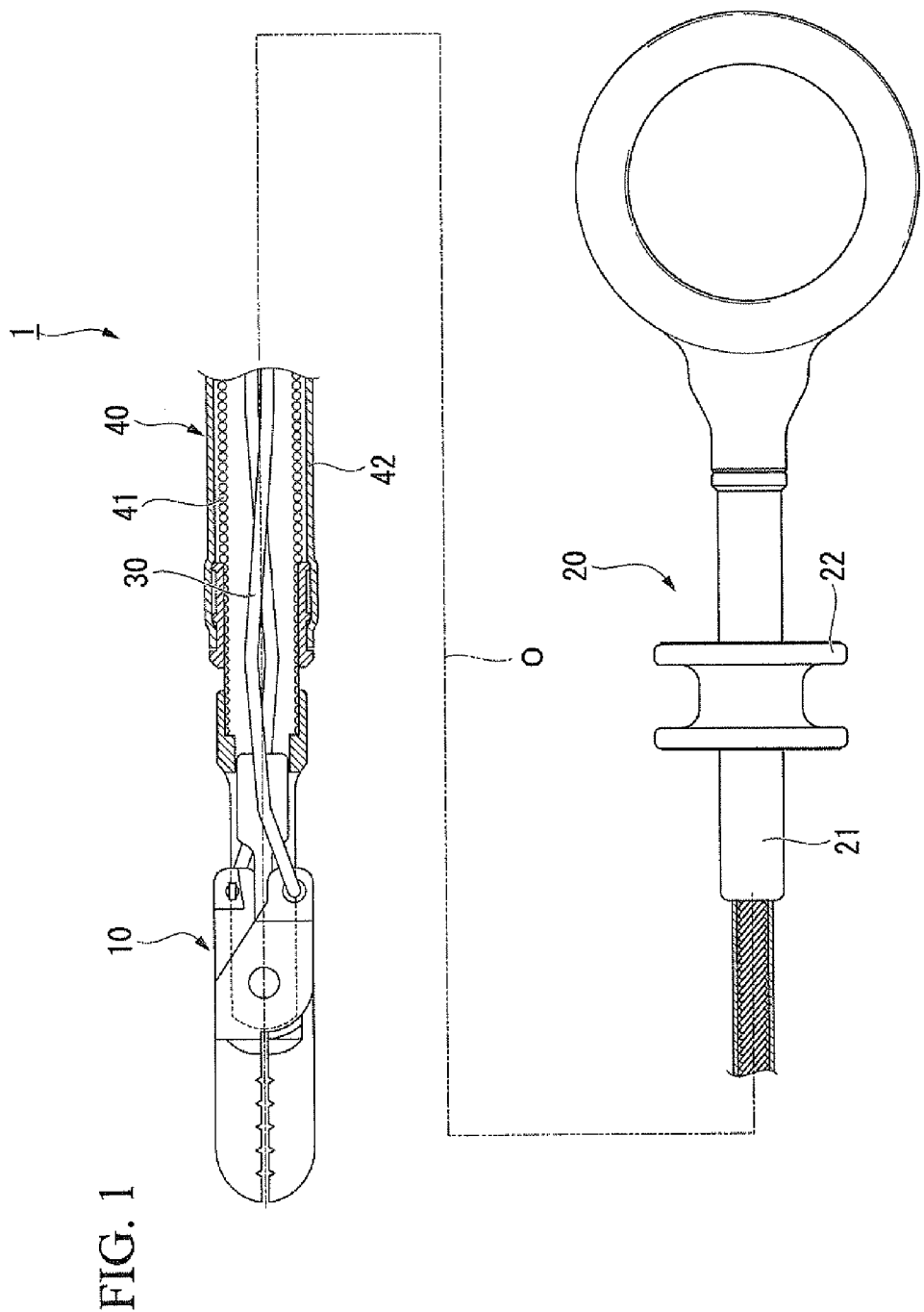
FIG. 1 is an overall view of a treatment device for an endoscope of one embodiment of the present invention.

A treatment device for an endoscope of one embodiment of the present invention will be described below with reference to FIGS. 1 to 8. As shown in FIG. 1, a treatment device for an endoscope (hereinafter simply referred to as "treatment device") 1 of the present embodiment includes a treatment part 10 for treating tissue within a body cavity, a manipulating part 20 for manipulating the treatment part 10, and two manipulation wires (manipulation shaft members) 30 that connect the treatment part 10 and the manipulating part 20, a coiled sheath part 40 through which the manipulation wires 30 are inserted so as to be able to advance and retract, and a fixing portion 48 that is arranged at the coiled sheath part 40.

Figure 2:
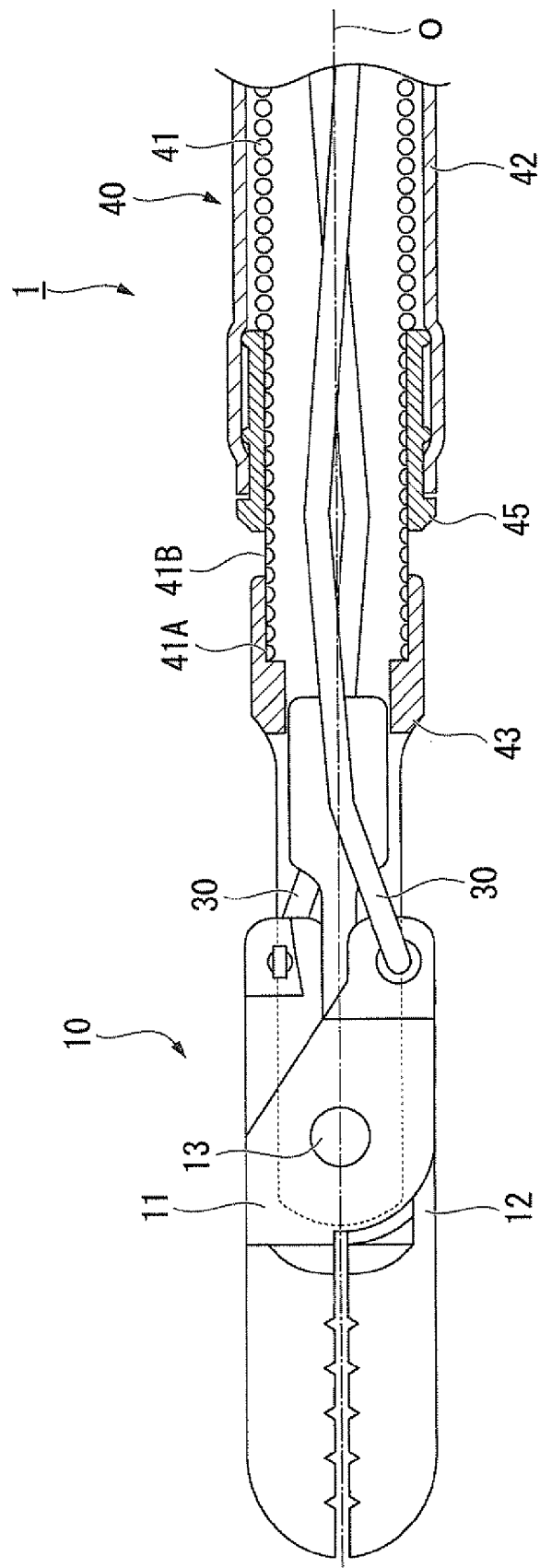
FIG. 2 is an exploded cross-sectional view of the treatment device for an endoscope on a distal end side.

FIG. 2 is an enlarged cross-sectional view of a distal end portion of the treatment device 1 including the treatment part 10. The treatment part 10 is configured by a pair of forceps members, that is, a first forceps member 11 and a second forceps member 12 that are rotatably coupled to each other by a rotation shaft 13. The manipulation wires 30 are connected closer to the proximal end side than the rotation shaft 13 of the respective forceps members 11 and 12, and the manipulation wires 30 are connected to the manipulating part 20 through the inside of the coiled sheath 40.

As shown in FIG. 1, the manipulating part 20 includes an elongated body 21, and a slider 22 attached to the body 21 so as to be slidable within a predetermined range in the direction of an axis O. The proximal ends of the manipulation wires 30 are inserted into the body 21, and are connected to the slider 22. Accordingly, by making the slider 22 slide with respect to the body 21, the manipulation wires 30 can be advanced and retracted to open and close the pair of forceps members 11 and 12.

The coiled sheath part 40, which is a part to be endoscopically inserted into a body cavity, includes a coiled sheath 41 through which the manipulation wires 30 are inserted, and a resinous tube 42 that covers the outer peripheral surface of the coiled sheath 41.

Figure 3:
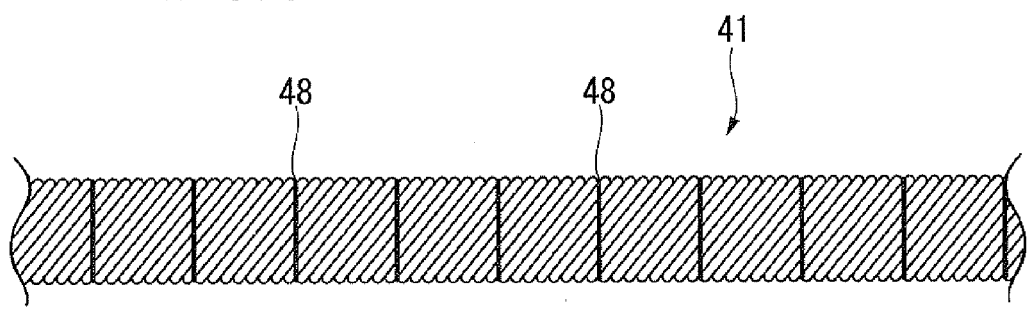
FIG. 3 is a drawing showing a coiled sheath of the treatment device for an endoscope.
Figure 4:
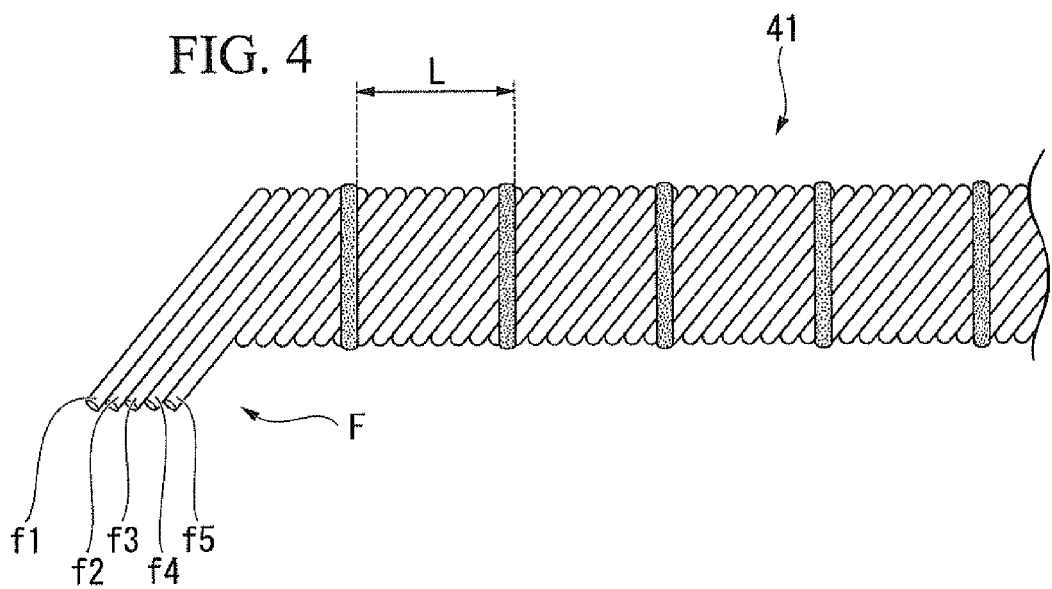
FIG. 4 is a view showing a winding method of the coiled sheath.

FIG. 3 is an outline view of the coiled sheath 41. The coiled sheath 41 is a long member formed by spirally winding metallic element wires. As shown in FIG. 4, the coiled sheath 41 is a so-called multi-wire coil sheath formed by densely winding a wire bundle, in which a plurality of element wires is arranged in the radial direction, in the shape of a loop. The number of element wires that are arranged in the radial direction is not particularly limited, and can be appropriately set. FIG. 4 shows a five-strip coiled sheath around which a wire bundle F is wound, as an example. As shown in FIG. 4, the wire bundle F has five element wires from an element wire f1 to an element wire f5, and these element wires f1 to f5 are arranged in the radial direction.

Furthermore, the treatment device 1 is provided with a plurality of the fixing portions 48. The plurality of fixing portions 48 that regulate a first relative movement between adjacent element wires is provided at intervals in the longitudinal direction in an intermediate portion between both ends of the coiled sheath 41 in the longitudinal direction. The plurality of fixing portions 48 is provided at intervals over almost the overall length of the sheath.

Figure 5A:
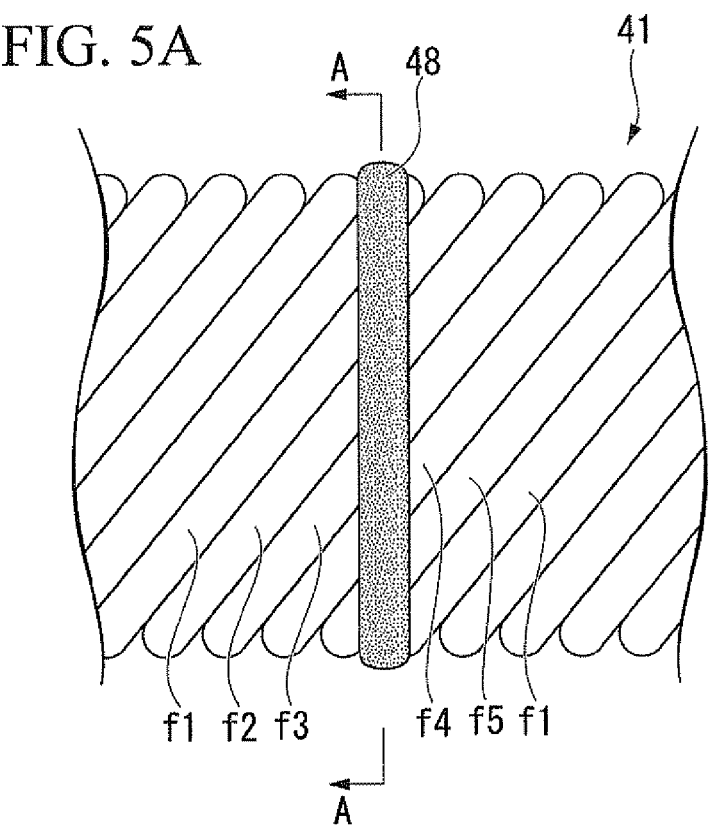
FIG. 5A is an enlarged view of a fixing portion of the coiled sheath.
Figure 5B:
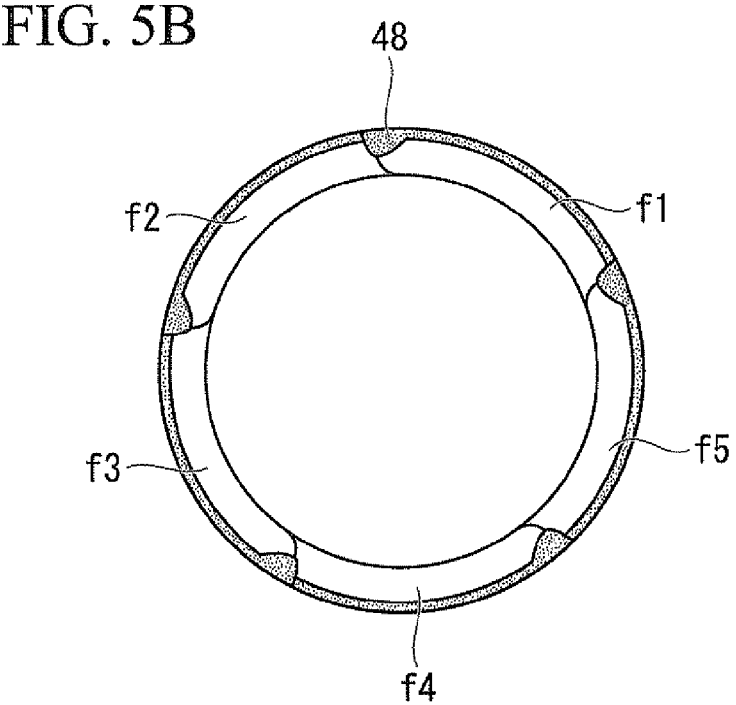
FIG. 5B is a cross-sectional view along line A-A of FIG. 5A.

FIG. 5A is an enlarged view of a fixing portion 48, and FIG. 5B is a cross-sectional view along line A-A of FIG. 5A. The fixing portion 48 is formed by performing laser welding in the circumferential direction of the coiled sheath 41. The element wires f1 to f5 that are arranged in the radial direction are fixed to each other by the fixing portion 48. Moreover, as shown in FIGS. 5A and 5B, the element wire f5 is also welded to the element wire f1 that is adjacent as the wire bundle F is wound in addition to the element wire f4. That is, in the fixing portion 48, parts of the wire bundle F that are adjacent as the wire bundle is wound in the shape of a loop as well as the element wires f1 to f5 that constitute the wire bundle F are fixed to each other. Thus, a second relative movement between adjoining parts is regulated.

As shown in FIG. 4, although the interval L between adjacent fixing portions 48 can be appropriately set, the interval is preferably 10 mm or more and 500 mm or less, and more preferably from 20 mm to 200 mm. As the interval between the fixing portions 48 is made smaller to provide a larger number of fixing portions, the suppressing effect of a displacement of the element wire to be described below is enhanced. However, the time required for manufacture of the coiled sheath is long, and flexibility is deteriorated. If the number of fixing portions is too small, the suppressing effect of the displacement of the element wires is reduced.

The interval between the fixing portions 48 may be regular intervals over the entire coiled sheath 41, and the interval may be different on different parts.

As shown in FIG. 2, a region with a predetermined length on a distal end 41A side of the coiled sheath 41 is worked by cutting or the like so as to have a flat outer peripheral surface 41B. A connecting member 43 for connecting the treatment part 10 and the coiled sheath part 40 is fixed to the distal end 41A of the coiled sheath 41 by welding or the like. The rotation shaft 13 is provided on the distal end side of the connecting member 43, so that the rotation shaft 13 is immovable relative to the connecting member 43.

A substantially tubular engaging member 45 is attached to the distal end side of the tube 42 by press-fitting or the like. The engaging member 45 engages with the proximal end side of the outer peripheral surface 41B the external diameter of which is made small by the above method. Although the proximal end of the tube 42 is inserted into the body 21 of the manipulating part 20, this proximal end is not fixed to the body 21, is movable in a predetermined range in the direction of the axis O relative to the manipulating part 20, and is relatively rotatable around the axis O.

On the other hand, since the proximal end of the coiled sheath 41 protrudes from the tube 42 and is fixed to the body 21, the tube 42 is rotatable around the axis O relative to the coiled sheath 41.

The operation when the treatment device 1 configured as described above is used will be described.

First, a user inserts the endoscope (not shown) into the body of a patient or the like, and advances the distal end of the endoscope to the vicinity of the target tissue in a body cavity to be treated (hereinafter referred to as "target tissue").

Subsequently, the user retracts the slider 22 with respect to the body 21 to bring the treatment part 10 into a closed state, and inserts the treatment part 10 and the coiled sheath part 40 of the treatment device 1 into a forceps channel (not shown) of the endoscope. Then, the treatment part 10 is made to protrude from the forceps channel.

When treatment is performed, the slider 22 is made to slide to the distal end side of the body 21. Then, the manipulation wires 30 connected to the slider 22 advance with respect to the coiled sheath part 40. As described above, since the rotation shaft 13 is immovable relative to the connecting member 43 attached to the distal end of the coiled sheath part 40, the first forceps member 11 and the second forceps member 12 rotate about the rotation shaft 13, respectively, and the treatment part 10 opens.

In a case where the opening and closing orientations of the forceps members 11 and 12 of the treatment part 10 that have protruded from the distal end of the endoscope are not suitable for the target tissue, the user grips the body 21 of the manipulating part 20 to rotate the body around the axis O while holding the tube 42. If the body 21 is rotated, the coiled sheath 41 and the treatment part 10 attached to the distal end of the coiled sheath 41 rotate around the axis O together with the body 21. In this way, the opening and closing orientations of the treatment part 10 can be adjusted. Since the treatment part 10 and the body 21 of the manipulating part 20 are connected by the coiled sheath 41, which is a multi-wire coil sheath, the torque generated by the rotational operation of the body 21 by the user as described above is favorably transmitted to the treatment part 10 by the coiled sheath 41. As a result, the treatment part 10 is rotated around the axis O while following the rotational operation of the body 21 favorably, so that the opening and closing orientations of the treatment part 10 can be easily performed.

If the user locates the target tissue between the opened forceps members 11 and 12 of the treatment part 10 and makes the slider 22 slide to the proximal end side of the body 21, the distal end side of the forceps members 11 and 12 is closed again, and the target tissue is grasped by the treatment part 10.

Generally, although the multi-wire coil sheath is excellent in torque transmissibility, there is a drawback in that the coiled sheath is inferior to resistance (resistance to compression) against the compressive force of a loop in the direction of the axis O. If a compressive force in the direction of the axis O acts on an ordinary multi-wire coil sheath, a so-called "displacement of the element wire" in which slippage occurs between element wires that constitute the multi-wire coil sheath may occur. Since the overall coiled sheath shrinks in the direction of the axis O if the displacement of the element wire occurs, a manipulation force for pulling the manipulation wires is absorbed, and transmission of the manipulation force to the treatment part reduces.

However, in the coiled sheath 41 of the present embodiment, the plurality of fixing portions 48 is provided at intervals at the intermediate portion between both ends. Therefore, even in a case where the displacement of the element wire occurs, the displacement of the element wire is limited to a region between the fixing portions. Accordingly, the overall coiled sheath does not shrink excessively even if a compressive force in the direction of the axis is received, and the manipulation force is favorably transmitted to the treatment part 10 when the manipulation wires 30 are pulled.

According to the treatment device 1 of the present embodiment, the coiled sheath 41 having the plurality of fixing portion 48 is used for the coiled sheath part 40. Therefore, even if two types of coiled sheaths are coaxially arranged as in the treatment device described in Japanese Unexamined Patent Application, First Publication No. 2008-212620, to balance a favorable rotational operation of the treatment part 10 and a favorable transmission of the manipulation force to the treatment part 10 can be achieved to a high level. As a result, it is possible to provide a treatment device for an endoscope in which torque transmissibility is high and a manipulation force is efficiently transmitted to the treatment part, while being capable of reduction in diameter.

Additionally, in the fixing portion 48, not only the respective element wires f1 to f5 of the wire bundle F are fixed to each other, but also the parts of the wire bundle F that are adjacent as being wound are fixed to each other. Accordingly, not only the displacement of the element wires f1 to f5, but also slippage between the parts of the wire bundle F can be suppressed, and a situation where the overall wire bundle causes the displacement can be favorably suppressed.

Moreover, since the fixing portion 48 is formed by performing laser welding in a circumferential direction of the coiled sheath, the fixing portion 48 can be easily formed.

Although an example in which the fixing portion is formed by laser welding has been described in the present embodiment, a method of forming the fixing portion is not limited to the above.

Figure 6:
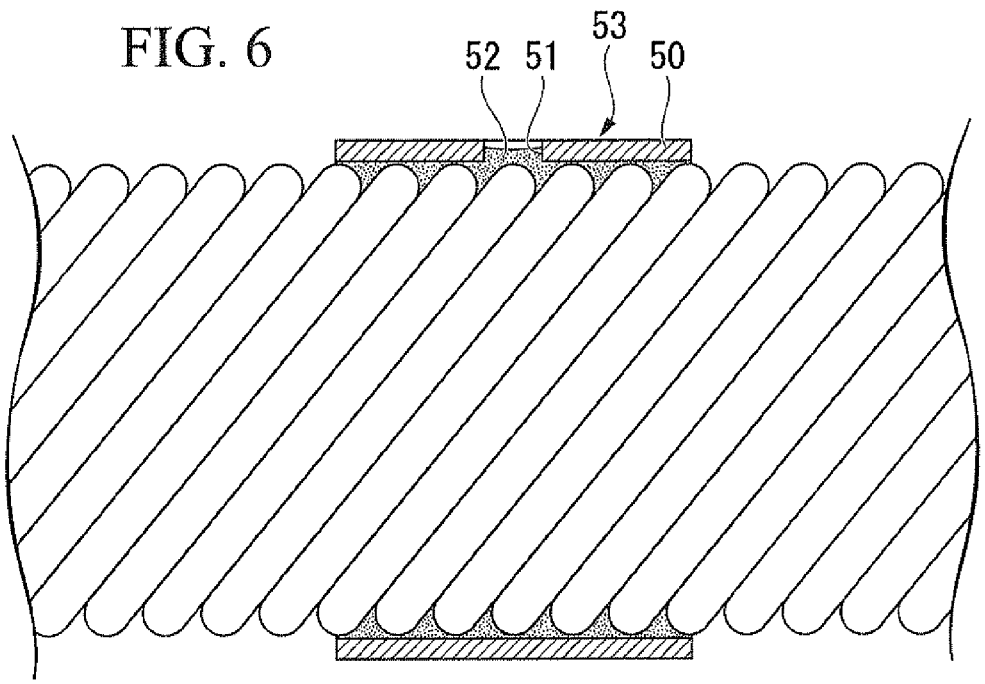
FIG. 6 is a view showing a fixing portion in a modification of one embodiment of the present invention.

For example, as in a modification shown in FIG. 6, a fixing portion 53 may be formed by attaching a pipe 50, having a through-hole 51 communicating with an inner cavity at the outer peripheral surface thereof, to the coiled sheath, and pouring a brazing material 52 from the through-hole 51. Additionally, although not shown, a fixing portion may be formed using pipes intermittently formed in the circumferential direction and having a slit communicating with an inner cavity, and soldering and welding the slit portion.

Figure 7:
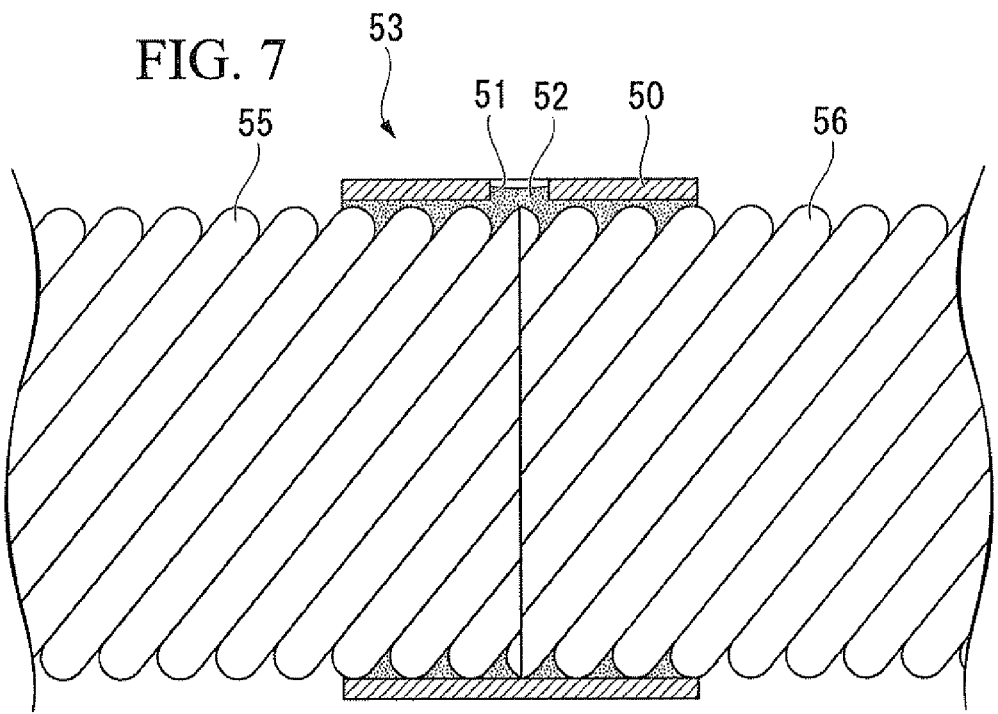
FIG. 7 is a view showing a fixing portion in a modification of one embodiment of the present invention.

Moreover, for example, particularly in a case where the coiled sheath part is long, the coiled sheath part may be configured by a plurality of multi-wire coil sheaths, and in a modification shown in FIG. 7, the above-described fixing may be formed at a connecting portion between a multi-wire coil sheath 55 and a multi-wire coil sheath 56. By using the plurality of multi-wire coil sheaths with a moderate length, there are advantages in that the space required for laser welding is small, a large-sized facility is less necessary, and assemblability is improved.

In addition, the fixing portion 48 using laser welding may be formed at a connecting part between the plurality of multi-wire coil sheaths.

Although one embodiment of the present invention has been described hitherto, the technical scope of the present invention is not limited to the above embodiment, and various modifications may be made without departing from the scope of the present invention.

Figure 8:
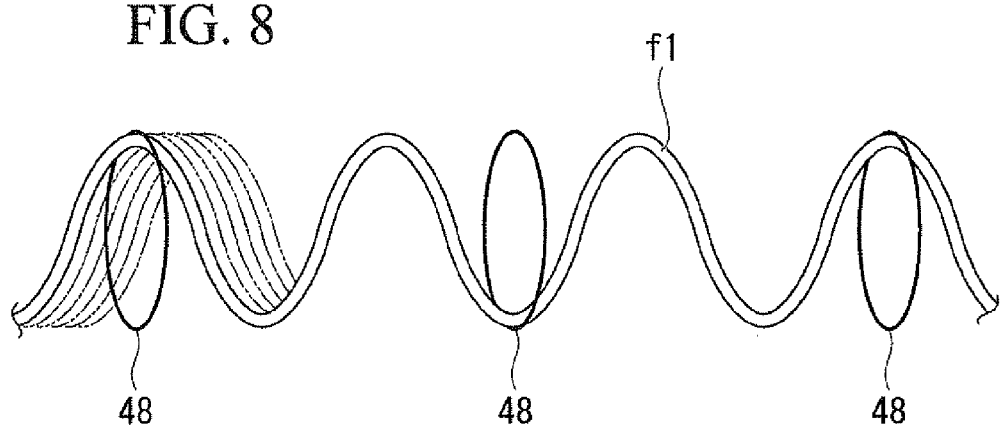
FIG. 8 is a view showing an example of element wires of the coiled sheath and the positions of fixing portions.
Figure 9:
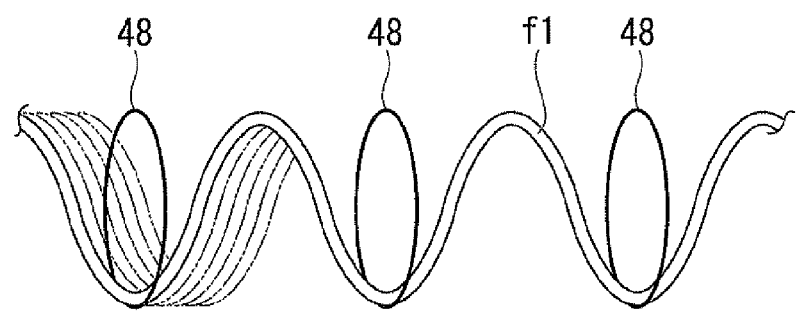
FIG. 9 is a view showing an example of element wires of the coiled sheath and the positions of the fixing portions.

FIGS. 8 and 9 are views showing the relationship between the positions where the fixing portions are provided, and loops of element wires. As shown in FIG. 8, attention is paid to a particular element wire (in FIG. 8, the element wire f1 is shown as an example) that forms a multiple coil. The fixing portions 48 may be provided so that the phase positions of parts, which are fixed by the fixing portions 48, in a loop formed by the element wire f1 are opposite each other across the axis of the loop in adjacent fixing portions 48. Then, the force that acts on the element wire f1 through the fixing portions 48 can be favorably decentralized in the circumferential direction of the coiled sheath. As a result, the fixing potions 48 neither make it easy nor difficult for the coiled sheath to curve in the specific direction. Even if the fixing portions may be provided so that the phases of parts fixed by the fixing portions displace by a predetermined degree of angle (for example, 90 degrees, 120 degrees, or the like) in adjacent fixing portions, the same effects can be obtained.

In contrast, as shown in FIG. 9, if the fixing portions are provided so that fixing using the fixing portions is performed in specific phase positions in the loop formed by the element wire f1, a coiled sheath that is hardly bent on the phase position side can be provided. Accordingly, the fixing portions are useful for, for example, a case where a treatment device that is easily bent in a specific direction is required.

Figure 10:
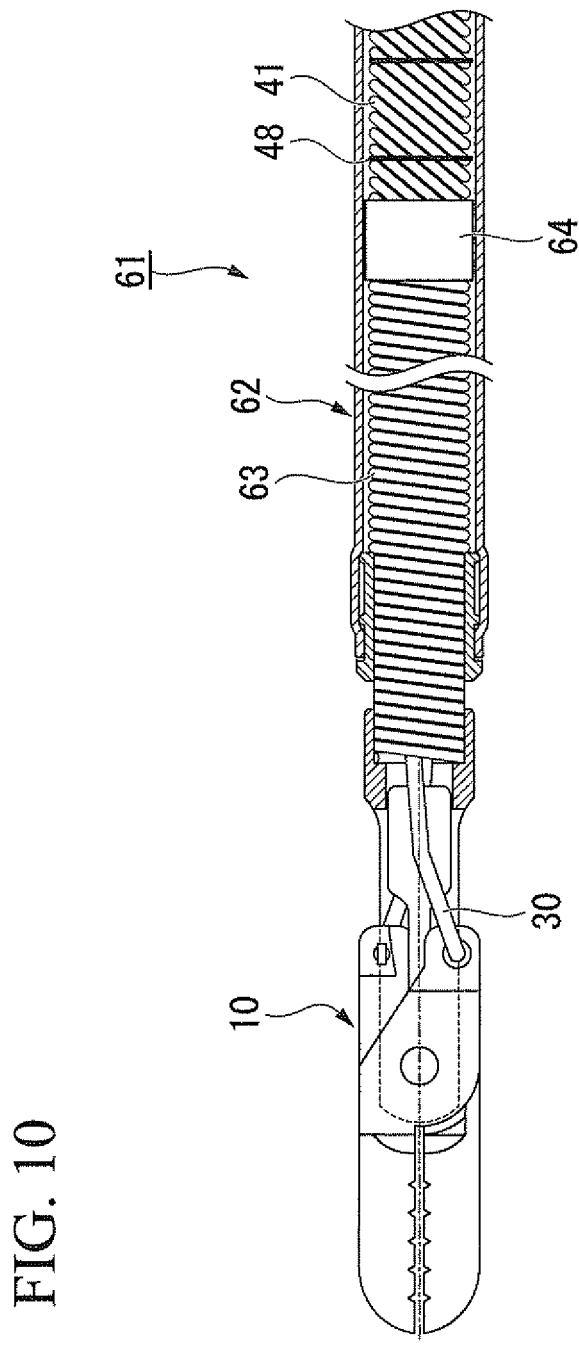
FIG. 10 is an enlarged view around a treatment part circumference in a treatment device for an endoscope of a modification of one embodiment of the present invention.

Additionally, although the fixing portions are provided over the overall length of the coiled sheath, the present invention is not limited to this, and a coiled sheath having the fixing portions at only a portion of the coiled sheath part (particularly, a required part) may be used. In a treatment device 61 for an endoscope of a modification shown in FIG. 10, a single-line coiled sheath 63 around which one element wire is wound is used for the region of the coiled sheath part 62 with a predetermined length on the treatment part 10 side that is curved by the curving manipulation of the endoscope. The coiled sheath 41 is connected to the proximal end side of the single-line coiled sheath 63 via a pipe 64. A treatment device that follows the curve of an endoscope to be inserted favorably and that also suppresses the displacement of the element wire can be provided by arranging the single-line coiled sheath 63 having excellent flexibility on the distal end side of the coiled sheath part 62.

Although the length of the single-line coiled sheath 63 can be appropriately set in consideration of an endoscope to be inserted or the like, if the length is set to be from 100 mm or more and to 300 mm or less, the coiled sheath can be favorably used for a number of endoscope apparatuses.

Figure 11:
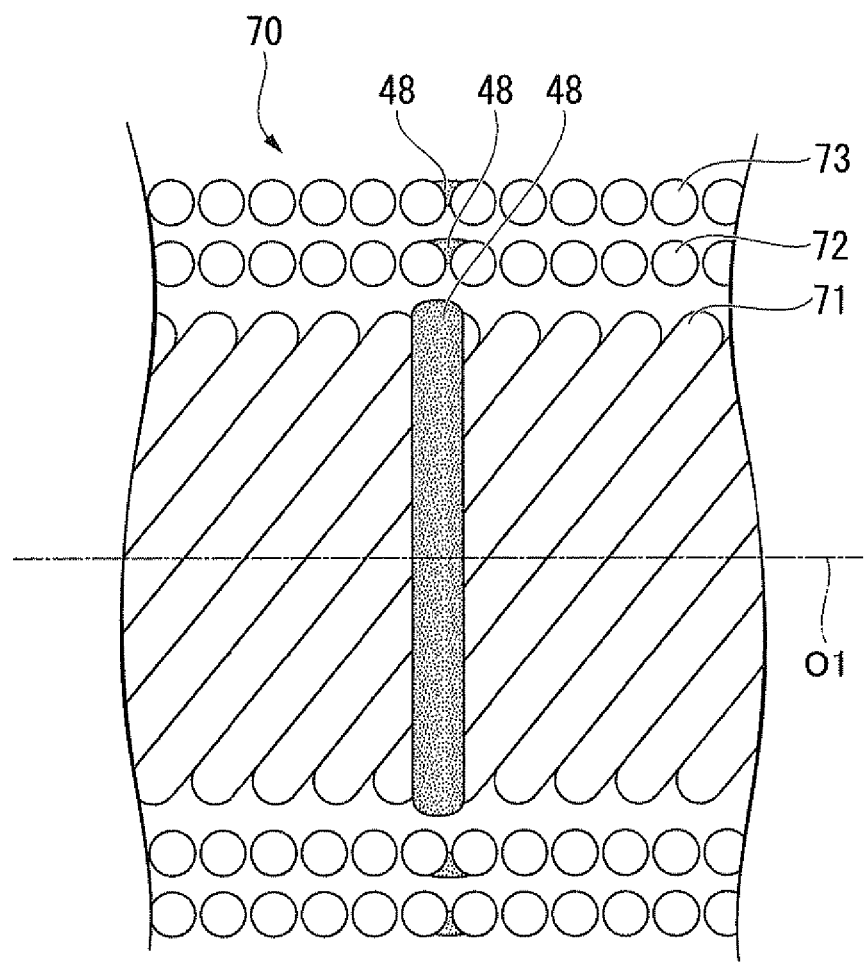
FIG. 11 is a cross-sectional view of a coiled sheath part in a modification of one embodiment of the present invention.

Additionally, for example, in a case where it is not necessary to reduce the diameter of the treatment device, the coiled sheath part may be formed using a multi-layer multi-wire coiled sheath 70 using coiled sheaths 71, 72, and 73 having the plurality of fixing portions 48 as a modification shown in FIG. 11. At this time, the positions of the fixing portions 48 of the respective coiled sheaths 71 to 73 in the multi-layer and multi-wire coiled sheath 70 may be the same in the direction of the axis O1 of the multiple multi-layer coiled sheath 70 as shown in FIG. 11, or may displace. Here, in the configuration in which the positions of the fixing portions displace, it may be to determine the interval between the fixing portions in consideration of the fixing portions of all the coiled sheaths.

Moreover, a coiled sheath part may be configured using a coiled sheath in which a coiled sheath having a plurality of fixing portions and a single-line coiled sheath are combined.

Moreover, although an example in which the manipulation wires are used as the manipulation shaft members has been described in the above-described embodiment, instead of this, the manipulation shaft members may be configured using rods or pipes or combining these.

In addition, although an example in which the treatment part includes a pair of forceps members has been described in the above-described embodiment, the treatment part in the treatment device of the present invention is not limited to this. That is, for example, a snare wire, so-called two-leg forceps, or the like can be applied to all treatment parts that need to adjust its orientation with respect to the target tissue to be treated.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

The invention claimed is:

1. A treatment device for an endoscope comprising:
   a treatment part that is adapted to treat tissue within a body cavity;
   a manipulating part that is adapted to manipulate the treatment part;
   a manipulation shaft member that connects the treatment part and the manipulating part;
   a multi-wire coil sheath that is formed by spirally winding a single continuous wire bundle having a plurality of adjacent element wires arranged in a longitudinal direction into a series of adjacent bundle turns, wherein the manipulation shaft member is inserted into the multi-wire coil sheath so that the manipulation shaft member is capable of being advanced and retracted; and
   a plurality of discrete fixing portions that are formed by performing welding over a circumferential direction of the multi-wire coil sheath and
   that are arranged at intervals in a longitudinal direction of the multi-wire coil sheath and between a distal end and a proximal end of the multi-wire coil sheath
   and that restrict a first relative movement between the adjacent element wires located in each of the plurality of discrete fixing portions and a second relative movement among each of the series of adjacent bundle turns of the single continuous wire bundle that are adjacent to each other and are located in each of the plurality of discrete fixing portions.

2. The treatment device for an endoscope according to claim 1, wherein the intervals between each of the plurality of the discrete fixing portions is between 10 mm and 500 mm.

3. The treatment device for an endoscope according to claim 1, wherein the plurality of the discrete fixing portions are formed by performing laser welding over a circumferential direction of the multi-wire coil sheath.

4. The treatment device for an endoscope according to claim 1, wherein the intervals of the plurality of the discrete fixing portions are provided over the overall length of the multi-wire coil sheath.

\* \* \* \* \*